US00PP28751P2

(12) United States Plant Patent
Hansen

(10) Patent No.: US PP28,751 P2
(45) Date of Patent: Dec. 5, 2017

(54) ***×HEUCHERELLA* PLANT NAMED 'RED ROVER'**

(50) Latin Name: *×Heucherella (Heuchera×Tiarella)*
Varietal Denomination: Red Rover

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 15/530,092

(22) Filed: Dec. 1, 2016

(51) Int. Cl.
*A01H 5/02* (2006.01)

(52) U.S. Cl.
USPC ..... Plt./441

(58) Field of Classification Search
USPC ..... Plt./441
CPC ..... A01H 5/02; A01H 5/12
See application file for complete search history.

*Primary Examiner* — Kent L Bell

(57) ABSTRACT

The new hybrid ×*Heucherella* plant named 'Red Rover' with deeply-incised, thin, finger-like, and distinctly-separated, palmately lobed foliage of variable coloration starting in the spring as coppery-red with burgundy red centers, transitioning to bright red during flowering and dark olive green in winter. 'Red Rover' begins flowering in late spring with a creamy-white effect and continues sporadically through the summer. The new plant is suitable for landscaping en masse, as an accent or as a container plant.

1 Drawing Sheet

Botanical denomination: ×*Heucherella* (*Heuchera*× *Tiarella*).

Cultivar designation: 'Red Rover'.

BACKGROUND OF THE INVENTION

The present invention relates to a new and distinct intergeneric hybrid between Coral Bells and Foam Flower, both in the Saxifragaceae family and given the cultivar name of 'Red Rover' with the combined generic epithet ×*Heucherella.* ×*Heucherella* 'Red Rover' resulted from an intentional cross between the unreleased proprietary *Heuchera* hybrid known by the breeder code 12-120-01 (not patented) as the female or seed parent and the unreleased proprietary hybrid labeled 11-14 (not patented) as the male or pollen parent. The new plant was hybridized by the inventor at a wholesale perennial nursery in Zeeland, Mich., USA on Feb. 11, 2013 and harvested in the spring of 2013. The new plant passed the original evaluation in summer 2013 and was given the initial breeder code of 13-156-01. The new plant was selected from among many other crosses and ×*Heucherella* seedlings growing at the same nursery in Zeeland, Mich. which met the rigorous criteria of excellent foliage and habit established as breeding goals. ×*Heucherella* 'Red Rover' has been asexually propagated since 2014 by division of the rhizome at a nursery in Zeeland, Mich. and also by careful tissue culture propagation. The resultant asexually propagated plants have remained stable and exhibit the same characteristics as the original plant.

No plants of ×*Heucherella* 'Red Rover' have been sold, under this or any name, in this country or anywhere in the world, prior to the filing of this application, nor has any disclosure of the new plant been made prior to the filing of this application with the exception of that which may have been disclosed within one year of the filing of this application and was either derived directly or indirectly from the inventor.

BRIEF SUMMARY OF THE INVENTION

×*Heucherella* 'Red Rover' differs from its parents as well as all other ×*Heucherella* known to the applicant. Compared to the female parent, the new plant has creamy-white flowers, the foliage more deeply dissected with longer lobes, and the foliage color is more reddish-bronze. Compared to the male parent, the new plant has more reddish bronze foliage with deeper-cleft and rounded lobes and the flowers are creamy-white rather than light pink. The most similar cultivars include: ×*Heucherella* 'Burnished Bronze' U.S. Plant Pat. No. 12,159, 'Autumn Cascade' U.S. Plant Pat. No. 27,569 and 'Sweet Tea' U.S. Plant Pat. No. 21,296.

Compared to 'Sweet Tea', the new plant has deeper cleft foliage with more rounded lobes. Compared to 'Burnished Bronze' the new plant has more deeply cleft leaf blades with more rounded lobes, and the coloration is more bronze rather than the reddish of 'Burnished Bronze'. The new plant has foliage that is more deeply cleft with rounded lobes than 'Autumn Cascade', and the habit is more clumping and less trailing. Compared to the copending 'Hopscotch' U.S. Plant patent application Ser. No. 15/530,091 the foliage has more rounded lobes and the coloration is brighter red.

The new plant differs from all *Heuchera,* ×*Heucherella* and *Tiarella* known to the inventor in the following combined traits:

1. The foliage color of ×*Heucherella* 'Red Rover' is variable with the seasons starting in the spring as coppery-red with burgundy red centers.
2. Foliage is deeply-incised, thin, finger-like, and distinctly separated lobes having rounded apices.
3. Leaves transition from coppery-red to bright red and late in the season become dark olive green.
4. The flowers are creamy-white and tightly arranged on panicles just over the foliage with repeat flowering over an extended period from late spring through summer.

5. Habit is mounded with multiple tightly clustered shoots emerging at the base all season.
6. The plant is robust, seedless, compact and is more heat and sun tolerant than typical ×*Heucherella*.

BRIEF DESCRIPTION OF THE DRAWINGS

The photographs of the new plant demonstrate the overall appearance of the plant including the unique trails. The plant in the photograph is of a two-year old plant grown in a shaded trial garden, with supplemental fertilizer and water as needed at a wholesale perennial nursery in Zeeland, Mich., USA. The colors are as accurate as reasonably possible with color reproductions. Some slight variation of color may occur as a result of lighting quality, intensity, wavelength, and direction or reflection.

DETAILED BOTANICAL DESCRIPTION

Figure 1:
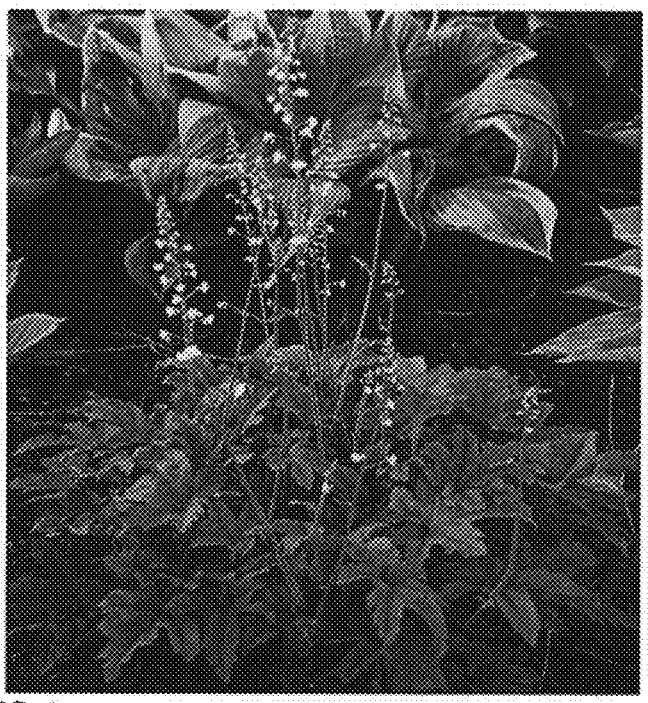
FIG. 1 shows a two-year-old plant in a shaded trial garden in Zeeland, Mich. in late spring flowering.
Figure 2:
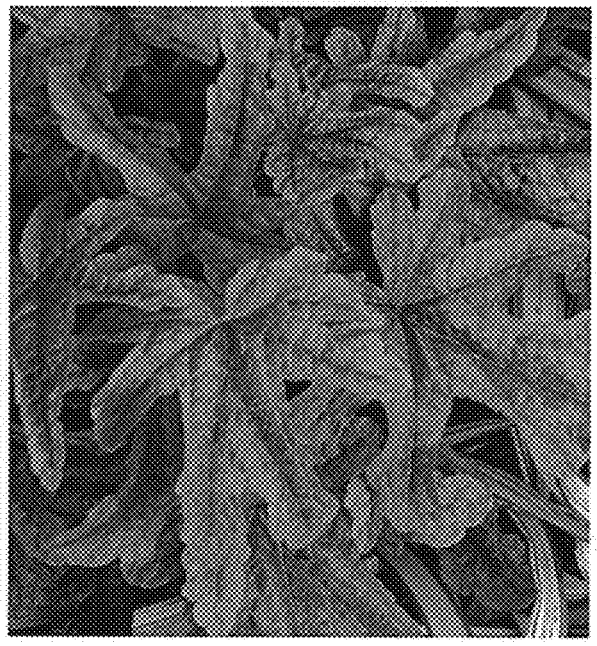
FIG. 2 shows a close-up of the foliage in mid-season coloration.

The following description is based on two-year-old plants growing in double poly greenhouse and two-year-old plants grown in an outdoor shaded trial garden with supplemental water and fertilizer at a wholesale perennial nursery in Zeeland, Mich., USA. The new plant has not been grown under all possible environments and may phenotypically appear different under different conditions such as light, temperatures, fertilizer, and water, without any difference in genotype. The color descriptions are from the 2001 edition of The Royal Horticultural Society Colour Chart except where common dictionary terms are used.

Parentage: Unreleased proprietary *Heuchera* hybrid 12-120-01 as the female (seed parent); the unreleased proprietary *Tiarella* hybrid labeled 11-14 (not patented) as the male (pollen parent); the female parent consists of a cross of 'Mocha' U.S. Plant Pat. No. 18,386 times *Heuchera hallii*.

Plant habit: Hardy herbaceous perennial of tightly compact rhizomes with basal rosette of mounded foliage; foliage about 20 cm tall and 40 cm in diameter.

Roots: Fibrous, finely branched; when actively growing near white in color depending on soil type.

Growth rate: Rapid, rooting from cutting in 2 weeks and finishing in three-liter container in about 3 months; beginning to flower in 6 to 8 weeks following a 9 week vernalization.

Foliage: Leaf blade puberulent above and sparsely puberulent below; palmately five-lobed, apical lobes incised typically to nearly four-fifths of the way to petiole; matte surface above and slightly lustrous below; rounded lobe apices with apices and margin ciliate, and cordate base with lobes imbricate to about 1.0 cm; blade to about 14.5 cm long and 12.5 cm wide, average about 12.5 cm long and 10.0 cm wide; center lobe to about 7.5 cm long and 6.0 cm wide at widest point; average about 5.5 cm long and about 5.0 wide; average separation between main lobe and side lobes about 2.2 cm at narrowest point.

Foliage color: Leaf color is seasonally variable; young spring and expanding leaves adaxial nearest RHS 183C; expanding abaxial nearest RHS 187C; at flowering and mid-season adaxial nearest RHS 183A with a burgundy center nearest RHS N186C, at flowering and mid-season abaxial between RHS 187C and RHS 187D; winter leaves adaxial mixtures of a blend between RHS 187A and RHS 189A, and a blend between RHS 139A and RHS 147A.

Leaf margin: Crenate to ciliate.

Leaf apex: Minutely pungent.

Leaf base: Cordate with frequently imbricate basal lobes.

Leaf surface: Puberulent adaxial and sparsely puberulent abaxial.

Leaf quantity: Dense, about eight to ten per division and 50 per plant.

Veins: Palmate, puberulent to pubescent adaxial and puberulent abaxial.

Vein color: Adaxial expanding foliage nearest RHS 185A and abaxial blend between RHS 183A and RHS N186D; at time of flowering and mid-season adaxial nearest RHS 182B, at time of flowering and mid-season abaxial main veins nearest RHS 187B; winter adaxial veins nearest RHS 176C and overwintered abaxial between RHS 176B and RHS 183A.

Petiole: Terete, pubescent, base clasping; to 10.0 cm long and 3.0 mm diameter base; average about 9.0 cm long and 2.5 mm diameter at base; wiry but flexible.

Petiole color: On emerging foliage between RHS 186A and RHS N186D; at flowering and mid-season nearest RHS N186D; winter between RHS 187A and RHS N187A.

Inflorescence: In tightly-banched panicle, about 16 racemes per plant; about 90 flowers per panicle; first panicle flowering beginning in late spring with repeat racemes flowering into summer; individual panicles remaining in flower for about three to four weeks; flower attitude mostly outwards.

Fragrance: None detected.

Peduncle: Terete, erect; glandular, puberulent; to about 60.0 cm tall and about 3.0 mm diameter at base; flowering portion about 30.0 cm long and about 6.0 mm across.

Peduncle attitude: Upright erect.

Peduncle branches: 20 branches per panicle; extending between 15 to 45 degrees above horizontal; branches to about 3.5 cm long and about 0.7 mm diameter at base.

Peduncle color: Between RHS N186C and RHS N186D.

Pedicel: Terete; puberulent to glandular; to about 4.0 mm long and 0.5 mm in diameter, average about 3.0 mm long and 0.5 mm diameter at base.

Pedicel color: Between RHS N186A and RHS N186C.

Buds one day prior to opening: Ellipsoid with rounded apex and rounded base; glandular to pubescent; about 3.0 mm long and 2.0 mm diameter.

Bud color: Lighter than RHS 186D.

Flower: Perfect, campanulate, actinomorphic; about 5.0 mm deep and 8.0 mm in diameter at face; individual flowers lasting about three to four days on plant or as cut raceme.

Calyx: Five sepals; glandular abaxial, glabrous adaxial; apex acute, fused at base into hypanthium; margin entire; sepals about 5.0 mm long and 1.5 mm wide at point of fusion.

Calyx color: Abaxial white, lighter than RHS 155D with glandular hairs the same color; adaxial near white nearest RHS 155D.

Petals: Five; adnate to calyx; spatulate, acute apex, attenuate base; margin entire; puberulent outside and glabrous inside; about 4.5 mm long and 0.8 mm wide at widest point.

Petal color: Abaxial and adaxial white, lighter than RHS 155D.

Androecium:

*Filaments*.—Five, thin, about 2.0 mm long and less than 0.5 mm in diameter; color white, lighter than RHS N155D.

*Anthers*.—Basifixed; oblong to about 0.5 mm long and about 0.2 mm wide; color nearest RHS 23D.

*Pollen*.—Not observed under present conditions.

Gynoecium:

*Pistil*.—One central two-beaked pistil.

*Style*.—About 5.0 mm long and 0.2 mm at apex flaring to 2.0 mm at base; color white, lighter than RHS 155D.

*Stigma*.—Minute, about 0.2 mm diameter; color nearest RHS 155D.

*Ovary*.—Two carpels; ovoid, apex tapering to meet style; rounded base and sides; about 2.0 mm across at base and 2.5 mm tall; color nearest RHS 155D.

Fruit and seed: Sterile; not observed.

Disease and pest tolerance: ×*Heucherella* 'Red Rover' grows best with ample moisture and good drainage in part shade or protection from sun in the hottest part of the day. Cold hardy from USDA zones 4 to 9. ×*Heucherella* 'Red Rover' is able to tolerate heat and humidity better than many ×*Heucherella*. Other pest and disease resistance and tolerance outside of that normal for ×*Heucherella* is not known.

It is claimed:

1. A new and distinct ornamental ×*Heucherella* plant named 'Red Rover' as herein illustrated and described.

* * * * *